US00RE35595E

United States Patent [19]

Six

[11] E Patent Number: Re. 35,595

[45] Reissued Date of Patent: Aug. 26, 1997

[54] FLEXIBLE TIP STYLET FOR USE WITH AN ENDOTRACHEAL INTUBATION DEVICE

[76] Inventor: Gary Six, 710 E. McHarg, Stamford, Tex. 79553

[21] Appl. No.: 140,541

[22] Filed: Oct. 21, 1993

Related U.S. Patent Documents

Reissue of:

[64] Patent No.: 5,058,577
Issued: Oct. 22, 1991
Appl. No.: 349,444
Filed: May 9, 1989

[51] Int. Cl.[6] ..... A61M 16/00

[52] U.S. Cl. ..... 128/200.26; 128/207.14; 128/207.15

[58] Field of Search ..... 128/200.26, 207.14, 128207.15, 4, 6, 11

[56] References Cited

U.S. PATENT DOCUMENTS

| | | | |
|---|---|---|---|
| 2,463,149 | 3/1949 | Caine | 128/349 |
| 2,541,402 | 2/1951 | Caine | 128/351 |
| 2,862,498 | 12/1958 | Weekes | 128/351 |
| 2,912,982 | 11/1959 | Barsky | 128/351 |
| 3,060,972 | 10/1962 | Sheldon | 138/120 |
| 3,314,431 | 4/1967 | Smith, Jr. | 128/351 |
| 3,402,718 | 9/1968 | Doherty | 128/351 |
| 3,416,531 | 12/1968 | Edwards | 128/348 |
| 3,443,564 | 5/1969 | Oehmig | 128/351 |
| 3,503,385 | 3/1970 | Stevens | 128/2 |
| 3,734,094 | 5/1973 | Calinog | 128/206 |
| 3,754,554 | 8/1973 | Felbarg | 128/351 |
| 3,776,222 | 12/1973 | Smiddy | 128/6 |
| 3,802,440 | 4/1974 | Salem et al. | 128/351 |
| 3,854,473 | 12/1974 | Matsuo | 128/8 |
| 3,957,055 | 5/1976 | Linder et al. | 128/351 |
| 3,996,939 | 12/1976 | Sheridan et al. | 128/351 |
| 4,050,466 | 9/1977 | Koerbacher | 128/351 |
| 4,146,019 | 3/1979 | Bass et al. | 128/6 |
| 4,150,676 | 4/1979 | Jackson | 128/351 |
| 4,244,362 | 1/1981 | Anderson | 128/200 |
| 4,275,724 | 6/1981 | Behrstock | 128/207 |
| 4,304,228 | 12/1981 | Depel | 128/200 |
| 4,329,983 | 5/1982 | Fletcher | 128/207 |
| 4,502,482 | 3/1985 | DeLuccia et al. | 128/207 |
| 4,529,400 | 7/1985 | Scholten | 604/95 |
| 4,553,540 | 11/1985 | Straith | 128/200 |
| 4,584,998 | 4/1986 | McGrail | 128/604 |
| 4,595,005 | 6/1986 | Jinotti | 128/205 |
| 4,655,214 | 4/1987 | Linder | 128/207 |
| 4,685,457 | 8/1987 | Donenfeld | 128/207 |
| 4,699,138 | 10/1987 | Behrstock | 128/207 |
| 4,762,125 | 8/1988 | Leiman et al. | 128/207 |
| 4,840,173 | 6/1989 | Porter, III | 128/207 |
| 4,846,153 | 7/1989 | Berci | 128/6 |
| 4,865,586 | 9/1989 | Hedberg | 604/93 |
| 4,878,900 | 11/1989 | Sundt | 604/119 |
| 4,881,761 | 11/1989 | Hornlein et al. | 285/239 |
| 4,892,095 | 1/1990 | Nakhgevany | 128/207 |
| 4,895,561 | 1/1990 | Mahurkar | 604/43 |
| 5,000,175 | 3/1991 | Pue | 128/207 |
| 5,329,940 | 7/1994 | Adair | 128/200.26 |

*Primary Examiner*—Aaron J. Lewis
*Attorney, Agent, or Firm*—Hopkins & Thomas

[57] ABSTRACT

An intubation tube stylet (10) is slidably received within an intubation tube (14). The stylet (10) comprises a handle (34), a flexible tube (24) and a performed tip (18) affixed to the flexible tube (24) such that the tip (18) extends beyond an insertion end (28) of the intubation tube (14). The flexible tip (18) comprises a general Z-Shape designed to facilitate insertion into the larynx and vocal cords of a patient regardless of any obstructing physical characteristics. Once the tip (18) is within the larynx, a plunger and cap (32), which is interconnected to a rod (30) through the handle (34), is activated to straighten the tip (18) allowing the intubation tube (14) to slide there along into the larynx. After the intubation tube (14) is within the larnx, the stylet (10) is removed to allow use of the intubation tube (14). The stylet (10) also provides for suction of the airway during insertion of the intubation tube (14) without the necessity of looking away from the insertion. Suction is provided by covering an opening (44) on the handle (34) which enables an external suction line (40) to draw materials through the tip (18), into the flexible tube (24), through the handle (34) and out the suction line (40).

16 Claims, 2 Drawing Sheets

FLEXIBLE TIP STYLET FOR USE WITH AN ENDOTRACHEAL INTUBATION DEVICE

Matter enclosed in heavy brackets [ ] appears in the original patent but forms no part of this reissue specification; matter printed in italics indicates the additions made by reissue.

TECHNICAL FIELD OF THE INVENTION

This invention relates in general to medical devices, and in particular to a flexible tip stylet for use with an endotracheal intubation device.

BACKGROUND OF THE INVENTION

In a variety of medical situations, it is necessary to place a ventilator tube through a patient's mouth and into the trachea in a procedure known as intubation. During this process, the ventilator tube must be negotiated over the tongue, past the epiglottis and through the vocal cords while avoiding the esophagus. For a variety of anatomical reasons, this procedure can often be extremely difficult. For example, a difficult intubation may be anticipated in patients with short muscular necks, receding jaws, large thick tongues, high arched palates, cervical spine or mandibular immobility, hematoma, abscess or inflammation around the posterior pharynx or larynx, facial fractures or anatomical deviations from normal. In addition, many ambulance personnel and paramedics are poorly trained and inexperienced in using an intubation device. Thus, whenever there is a difficult intubation, the patient may suffer damage to internal organs.

Prior attempts to alleviate the difficulties inherent with intubations have not resulted in satisfactory solutions. For example, one previous method disclosed in U.S. Pat. No. 3,996,939 to Sheridan et al., Dec. 14, 1976, is a bendable wire around which the intubation tube is placed. A wire or metal rod is hermetically sealed in a tubular plastic sheath, which is then inserted into the intubator. The metal wire is then bent to the appropriate shape for insertion, which often requires several attempts. For difficult situations, these devices are tedious to use and can slow a procedure in which speed of completion is often critical in nature.

Further attempts to alleviate the difficulties of intubation are disclosed in U.S. Pat. No. 2,541,402 to Caine, Feb. 13, 1951, and U.S. Pat. No. 3,314,431 to Smith, Apr. 18, 1967. The Caine and Smith patents both disclose stylets that have a bendable tip which can be bent while the stylet is being inserted into the throat of a patient. The purpose of the remote bending is to attempt to help the insertion by maneuvering around the internal obstructions. Unfortunately, both the Caine and the Smith devices do not provide adequate flexibility to easily maneuver past all the potential internal obstructions.

In a related problem during intubation, it is frequently necessary to provide suction to the throat to remove any foreign objects such as blood or vomit. Previously it has been necessary for medical personnel inserting the intubation tube to take their eyes off the insertion process to obtain a suction device to clear the throat. Since it is such a difficult task to insert the intubation tube in the first place, any distraction makes the task more difficult.

An attempt to resolve the suction problem is disclosed in U.S. Pat. No. 4,275,724 to Behrstock, June 30, 1981. Behrstock discloses an inner tube surrounded by an outer tube. The inner tube may be used to suction materials from the airway by sucking on the end of the inner tube during the insertion of the outer tube. This method also requires the medical person inserting the tube to look away from the task at hand in order to suck on the end of the tube. Therefore, there is a need for an intubation tube stylet that is both easy to insert and allows for suction during the insertion thereof without the necessary of the operator looking away from the insertion process.

SUMMARY OF THE INVENTION

The present invention disclosed herein comprises a method and apparatus for an improved intubation stylet which eliminates or greatly reduces problems associated with prior intubation stylets. The present invention allows the easy insertion of an intubation tube into the airway of any patient and allows for simultaneous suction without looking away from the insertion.

In accordance with one aspect of the invention, a flexible stylet is slidably received within an intubation tube. The stylet has a tip extending beyond the insertion end of the intubation tube. The tip has a remotely adjustable, preformed shape which facilitates insertion of the intubation tube into the airway of a patient and does not require deformation of the intubation tube itself.

In a further aspect of the present invention, the preformed shape comprises a general Z-Shape in which a first portion lies along a linear axis of the stylet. A second portion is bent at an angle to the linear axis, and a third portion extends from the second portion approximately parallel to the linear axis to form the general Z-Shape. The stylet tip is adjustable from the Z-Shape to a linear shape by a plunger and a rod interconnected to the stylet tip through a handle. By activating the plunger, the interconnected rod is forced into the tip of the stylet, straightening the tip into a linear shape. The stylet may be inserted or removed from an intubation tube when the tip is forced into a linear shape, and the intubation tube may be inserted into the airway of a patient when the stylet tip is in the general Z-Shape.

Additionally, the handle for the stylet has a passageway therethrough to connect the tip of the stylet to a suction line. By a simple hand movement, the medical person inserting the intubation tube can apply suction without the necessity of looking away from the insertion.

The stylet is preferably formed from relatively inexpensive materials such as plastics. Although it is possible to use metallic parts, metal is used only where necessary in order to keep costs as low as possible. Thus the stylet may be used once and disposed of to prevent the spreading of disease therefrom.

It is a technical advantage of the present invention that a difficult intubation may be successfully made even by poorly trained medical personnel. Additionally, the improved stylet is easy to manufacture and is made from relatively low-cost materials, allowing the stylet to be disposed of after use. It is a further technical advantage of the present invention that is is possible to apply suction to the airway without the necessity of looking away from the insertion.

BRIEF DESCRIPTION OF THE DRAWINGS

For a more complete understanding of the present invention and for further advantages thereof, reference is now made to the following Detailed Description, taken in conjunction with the accompanying Drawings in which.

DETAILED DESCRIPTION OF THE INVENTION

Figure 1:
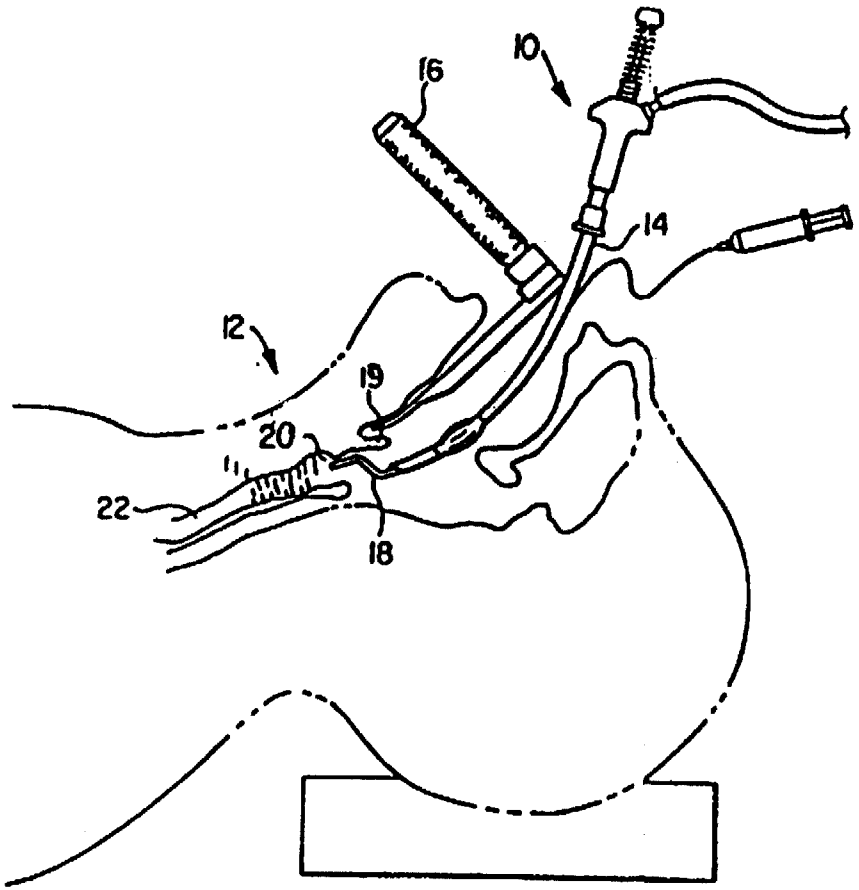
FIG. 1 is a plan view of an intubation tube about to be inserted into the airway of a patient using the improved intubation stylet of the present invention.
Figure 2:
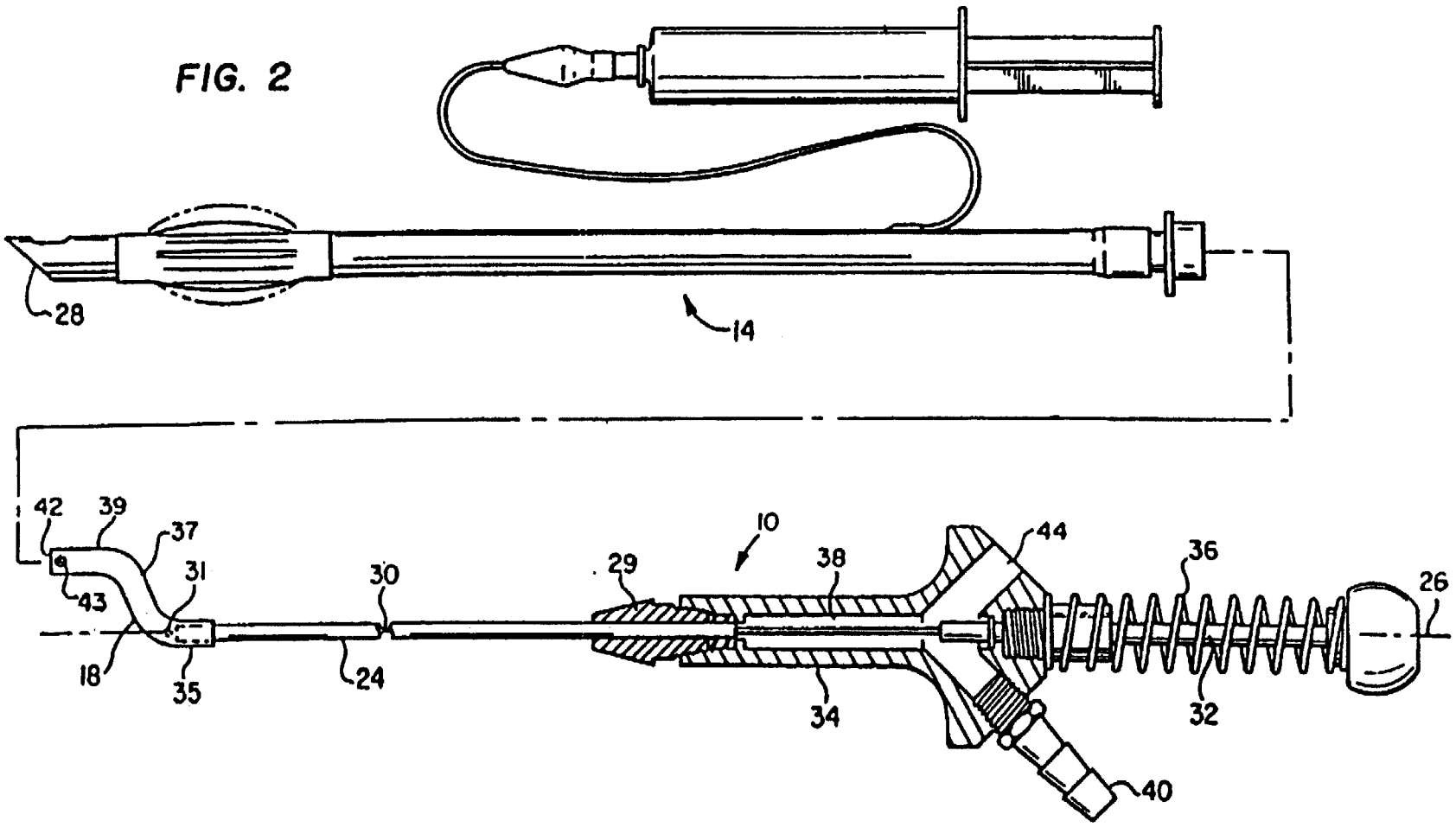
FIG. 2 is a cross-sectional view of the improved intubation stylet of the present invention.

In FIGS. 1–3, like items are identified by like and corresponding numerals for ease of reference. Referring to FIG. 1, a plan view of an improved intubation stylet constructed in accordance with the preferred embodiment of the present invention is generally identified by the reference numeral 10. Generally indicated by the reference numeral 12 is a cross-sectional view of the head and neck of a patient requiring intubation. The stylet 10 is used in conjunction with an intubation tube 14, which has been installed thereon. A laryngoscope 16 is initially inserted into the mouth and throat until the tip thereof lies behind the epiglottis 19.

After insertion of the laryngoscope 16, the stylet 10 and its attached intubation tube 14 are inserted into the mouth and throat of the patient 12. Due to the special shape (a general Z-Shape) of the preformed tip 18 of the stylet 10, it is possible to maneuver the stylet 10 past the vocal cords 20 and into the larynx 22. The tip 18 is preferably constructed from a plastic material which is capable of being permanently deformed into its special preformed shape and yet flexible enough to be straightened and then return to its preformed shape.

This insertion, which can be extremely difficult, depending upon the physical attributes of the patient 12, is easily facilitated because of the preformed shape of the tip 18 of the stylet 10. Minimal, if any, damage is done to the vocal cords 20 and the larynx 22 of the patient because the tip 18 is easily fitted therein. Once the tip 18 is inserted into the vocal cords 20, the stylet 10 is activated to allow insertion of the intubation tube 14 and removal of the stylet 10, as will be subsequently described in greater detail.

Referring to FIG. 2, the stylet 10 and the intubation tube 14 are shown in cross-sectional views. The intubation tube 14, which is of a standard construction well known in the art, is slidably received by a flexible tube 24 of the stylet 10. To install the intubation tube 14 over the tube 24, the preformed tip 18 must be straightened into an approximately linear shape along a linear axis 26 passing through the stylet 10, as will be subsequently described in greater detail. Once the intubation tube 14 is installed on the flexible tube 24, the preformed tip 18 extends beyond an insertion end 28 of the intubation tube 14.

The flexible tube 24 which may comprise aluminum or plastic is hollow with a rod 30 passing freely therethrough. The rod 30 which may comprise a metal wire is sufficiently flexible to bend with the flexible tube 24 yet stiff enough to straighten the preformed tip 18 when forced therein. The rod 30 does not completely fill the tube 24 to allow for suction and preferably has a tip protector 31 constructed and arranged to prevent damage to the preformed tip 18. The rod 30 is interconnected to a plunger and cap 32 through a handle 34 which may comprise aluminum or plastic and is constructed and arranged to comfortably receive an operator's hand. [The flexible tube 24 is affixed to the handle 34 by any appropriate method such as a connector 29.] Although not required, the plunger and cap 32 may be biased to keep the rod 30 out of the preformed tip 18 by a spring 36.

To install the stylet 10 into the intubation tube 14, the plunger 32 is pushed into the handle 34, forcing the rod 30 through the flexible tube 24 and into the preformed tip 18. As the rod 30 enters the preformed tip 18, the preformed tip 18 is forced into a linear shape along the linear axis 26. The stylet 10 is then inserted into the tube 14 until the preformed tip 18 protrudes from the insertion end 28. The plunger 32 is then released, allowing the rod 30 to be removed from the preformed tip 18, which then resumes its general Z-Shape. The intubation tube 14 and the stylet 10 are then ready for insertion into the airway of a patient.

The general Z-Shape of the preformed tip 18 is especially designed to provide quick and easy insertion into the vocal chords and larynx of a patient even if there are physical attributes or conditions that normally hinder insertion. For example, insertion would be extremely difficult if the patient had a short muscular neck, a receding jaw, a large thick tongue, a high arched palate, a cervical spine or mandibular immobility, an anterior larynx, a hematoma, an abscess or inflammation around the posterior pharynx or larynx, or a facial fracture or anatomical deviation from normal. The general Z-Shape of the tip 18 comprises a first portion 35 extending along the linear axis 26 and affixed to the tube 24. A second portion 37 is bent at an angle from the first portion 35, and a third portion 39 extends from the second portion 37 approximately parallel to the linear axis 26 and the first portion 35. It is to be understood that the exact angles of the bends between the three portion 35, 37 and 39 may vary as long as the general Z-Shape is maintained. Although not shown, it is to be understood that the open end 42 may have various other shapes such as angled.

Additionally, it is possible to suction out any foreign material in the airway during insertion of the intubation tube 14 by using the suction capabilities of the stylet 10. The handle 34 has a Y-Shaped internal channel 38 through which the rod 30 and the plunger 32 pass. The Y-Shape of channel 38 allows the insulation of a suction line 40 which is then directly in contact with an open end 42 of the preformed tip 18 through the flexible tube 24.

Opposite the suction line 40 is an opening 44 into the Y-Shaped channel 38, which is conveniently located in the handle 34. Once a suction line 40 is hooked to the handle 34, suction may be constantly available. However, due to the opening 44, there is no suction at the open end 42 of the preformed tip 18. To apply suction at the open end 42, an operator need merely cover the opening 44 with a thumb or finger, and suction of any foreign material may then be conducted through the open end 42, into the tip 18, through the flexible tube 24, and out the suction line 40.

The open end 42 of the tip 18 may have at least one hole 43 to allow suction from the side as well as through the open end 42. Thus, it is possible for an operator to insert an intubation tube 14 into the airway of a patient and simultaneously apply suction without the necessity of looking away from the insertion procedure.

Figure 3A:
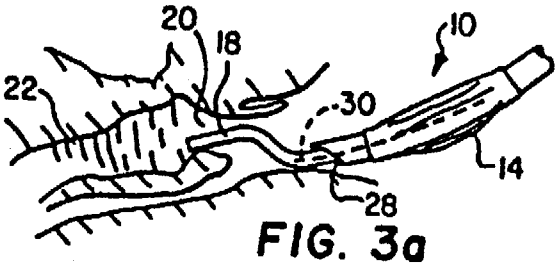
FIGS. 3a–c are partial side views of the insertion process using the preferred embodiment of the present invention.
Figure 3B:
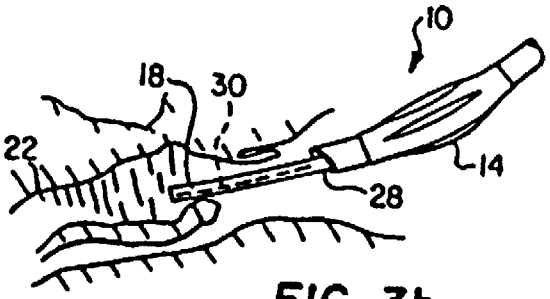
Figure 3C:
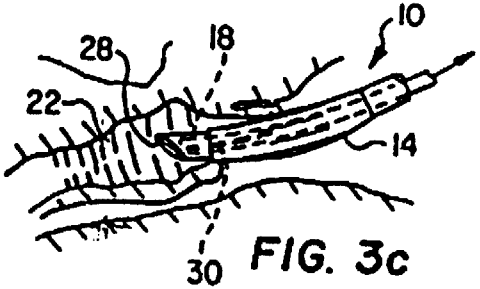

Referring to FIGS. 3a–3c, a method in accordance with the present invention for inserting an intubation tube into the larynx past the vocal cords of a patient is illustrated in cross-sectional view. Referring first to FIG. 3a, the stylet 10 and the intubation tube 14 have been inserted into the throat of a patient. The preformed tip 18 is shown entering the vocal cords 20 and the larynx 22. Due to the general Z-Shape of the preformed tip 18, the stylet 10 allows for easy insertion into the vocal cords 20 without harmful contact therebetween.

Referring to FIG. 3b, once the tip 18 has been inserted into the larynx 22, the plunger 32 (FIG. 2) is pushed into the handle 34 so that the rod 30 is forced into the tip 18. Forcing the rod 30 into the preformed tip 18 causes the tip 18 to be deformed from its general Z-Shape into a linear shape coextensive with the linear axis 26 of the stylet 10. From this position, with a straightened tip 18, the intubation tube 14 may easily slide past the tip 18 into the larynx 22 (FIG. 3c) without the need to deform the shape of the tube 14 itself. Once the insertion end 28 of the intubation tube 14 is inside the larynx 22, the stylet 10 may be removed from the intubation tube 14, leaving the intubation tube 14 properly installed into the airway of the patient.

Thus, an intubation tube can be inserted into the airway of a patient regardless of any difficult physical attributes of the patient, such as an anterior larynx. Due to its simple construction and its relatively inexpensive parts, the stylet 10 may be disposed of after use with a patient. It is no longer necessary to attempt an insertion, remove the stylet to change the shape thereof, attempt to insert again, remove the stylet for further modifications, and etc., until the stylet has been properly shaped for insertion into the airway. It is also no longer necessary to look away from the patient during the insertion process to obtain suction to remove any foreign material from the airway. A simple movement of the hand of the operator is all that is required to provide suction at any time.

Although the present invention has been described with respect to a specific preferred embodiment thereof, various changes and modifications may be suggested to one skilled in the art, and it is intended that the present invention encompass such changes and modifications as fall within the scope of the appended claims.

What is claimed is:

1. An improved intubation stylet, comprising:

a handle having a first and second end;

a flexible tube affixed to said first end of said handle, said tube having a remotely adjustable preshaped tip distal said handle, said preshaped tip comprising a first portion extending along a linear axis of said stylet, a second portion extending from said first potion and bent at an angle therefrom, and a third portion extending from said second portion and approximately parallel to said linear axis, said first, second and third portions forming a general Z-shape, said preshaped tip extending beyond an insertion end of an intubation tube such that said intubation tube does not conform to said general Z-shape during an intubation procedure;

a rod slidable received within said flexible tube, said rod terminating prior to said preshaped tip;

a plunger affixed to said rod through said handle, said plunger extending from said second end of said handle, such that as said plunger is pushed into said handle said rod passes through said flexible tube into said preshaped tip to deform said preshaped tip;

said handle having a Y-shaped channel passing therethrough, said Y-shaped channel being interconnected to said preshaped tip by said flexible tube to allow suction therethrough;

said handle further having a first opening in communication with said Y-Shape channel and arranged for connection to an external suction line; and said handle further having a second opening opposite said first opening and in communication with said Y-Shape channel to allow suction to be applied by covering said second opening.

2. The stylet of claim 1, wherein said plunger further comprises a spring to bias said plunger such that said rod allows said tip to remain in said preformed shape.

3. The stylet of claim 1, wherein said flexible tube comprises aluminum.

4. The stylet of claim 1, wherein said flexible tube comprises plastic.

5. The stylet of claim 1, wherein said preshaped tip comprises a plastic material.

6. The stylet of claim 1, wherein said rod comprises a metal wire.

7. The stylet of claim 1, wherein said rod further comprises a tip protector to prevent damage to said preshaped tip.

8. The stylet of claim 1, wherein said handle comprises aluminum.

*9. A method for performing an endotracheal intubation, comprising the steps of:*

*providing a suction tube, comprising a flexible tip and a stylet, in an intubation tube such that said suction tube is operative to aspirate fluids through said flexible tip from a location adjacent a distal end of said intubation tube; and*

*guiding said suction tube and said intubation tube simultaneously through the trachea of a patient by manipulating said stylet to deform said suction tube, said suction tube being operative to clear said trachea of fluids and secretions as said suction tube and said intubation tube are advanced through said trachea.*

*10. A method for performing an endotracheal intubation, comprising the steps of:*

*providing a suction tube having a stylet therein and having a flexible tip within an intubation tube such that said suction tube is operative to aspirate fluids through said flexible tip from a location adjacent a distal end of said intubation tube; and*

*guiding said suction tube and said intubation tube simultaneously through the trachea of a patient by manipulating said stylet to deform said suction tube, said suction tube being operative to clear said trachea of fluids and secretions as said suction tube and said intubation tube are advanced through said trachea.*

*11. The method of claim 10, further comprising the step of, subsequent to said step of introducing said suction tube and said intubation tube simultaneously through the trachea of a patient, withdrawing said suction tube from said patient, leaving said intubation tube in place within the trachea of said patient.*

*12. The method of claim 10, wherein said step of positioning said suction tube within said intubation tube comprises sliding said suction stylet into said intubation tube such that said suction stylet is slidably received within said intubation tube.*

*13. The method of claim 12, comprising the further steps of, subsequent to said step of introducing said suction tube and said intubation tube simultaneously through the trachea of a patient, disengaging said suction tube from said intubation tube and withdrawing said suction tube from said patient, leaving said intubation tube in place within the trachea of said patient.*

*14. The method of claim 10, wherein said step of positioning said suction tube within said intubation tube comprises sliding said suction tube into said intubation tube such that said suction tube is releasably axially fixed within said intubation tube.*

*15. The method of claim 14, comprising the further steps of, subsequent to said step of introducing said suction tube and said intubation tube simultaneously through the trachea of a patient, disengaging said suction tube from said intubation tube and withdrawing said suction tube from said*

*patient, leaving said intubation tube in place within the trachea of said patient.*

*16. The method of claim 10, wherein said step of positioning said suction tube within said intubation tube comprises the step of positioning said suction tube within said intubation tube, and comprising the further step of adjusting said suction tube to a desired shape prior to said step of introducing said suction tube and said intubation tube simultaneously through said trachea so as to facilitate passage of said suction tube and said intubation tube through said trachea.*

* * * * *